United States Patent
Hou et al.

(10) Patent No.: US 12,371,509 B2
(45) Date of Patent: Jul. 29, 2025

(54) ANTIBODIES SPECIFIC TO MUC18

(71) Applicant: Multitude Inc., Shanghai (CN)

(72) Inventors: Bing Hou, Shanghai (CN); Peng Chen, Shanghai (CN); Junli Liu, Shanghai (CN); Shu-Hui Liu, Redwood City, CA (US); Xun Meng, Shanghai (CN)

(73) Assignee: Multitude Inc., Shanghai (CN)

( * ) Notice: Subject to any disclaimer, the term of this patent is extended or adjusted under 35 U.S.C. 154(b) by 1015 days.

(21) Appl. No.: 17/350,995

(22) Filed: Jun. 17, 2021

(65) Prior Publication Data

US 2022/0041748 A1 Feb. 10, 2022

Related U.S. Application Data

(63) Continuation of application No. PCT/US2019/067387, filed on Dec. 19, 2019.

(30) Foreign Application Priority Data

Dec. 21, 2018 (WO) ................ PCT/CN2018/122567

(51) Int. Cl.
| | | |
|---|---|---|
| C07K 16/00 | (2006.01) | |
| A61K 40/11 | (2025.01) | |
| A61K 40/31 | (2025.01) | |
| A61K 40/42 | (2025.01) | |
| C07K 14/705 | (2006.01) | |
| C07K 14/725 | (2006.01) | |
| C07K 16/30 | (2006.01) | |
| A61K 39/00 | (2006.01) | |

(52) U.S. Cl.
CPC .......... C07K 16/3092 (2013.01); A61K 40/11 (2025.01); A61K 40/31 (2025.01); A61K 40/4257 (2025.01); A61K 40/4271 (2025.01); C07K 14/7051 (2013.01); C07K 14/70517 (2013.01); C07K 14/70521 (2013.01); A61K 2039/505 (2013.01); A61K 2239/13 (2023.05); A61K 2239/31 (2023.05); A61K 2239/38 (2023.05); A61K 2239/57 (2023.05); C07K 2317/565 (2013.01); C07K 2319/02 (2013.01); C07K 2319/03 (2013.01); C07K 2319/30 (2013.01); C07K 2319/33 (2013.01)

(58) Field of Classification Search
None
See application file for complete search history.

(56) References Cited

U.S. PATENT DOCUMENTS

| 6,824,995 B1 | 11/2004 | Wu |
| 2003/0147809 A1 | 8/2003 | Gudas |
| 2003/0152514 A1 | 8/2003 | Gudas |
| 2012/0121598 A1 | 5/2012 | Boumsell et al. |
| 2014/0105899 A1 | 4/2014 | Lin et al. |
| 2014/0227292 A1 | 8/2014 | Flanagan et al. |
| 2018/0271994 A1* | 9/2018 | Nejatollahi ........ A61K 47/6829 |
| 2022/0041749 A1 | 2/2022 | Hou et al. |

FOREIGN PATENT DOCUMENTS

| CN | 101245101 A | | 8/2008 | |
| CN | 104650231 A | | 5/2015 | |
| CN | 108129567 A | * | 6/2018 | ......... C07K 16/3092 |
| JP | 2005-514425 A | | 5/2005 | |
| JP | 2017-518258 A | | 7/2017 | |
| WO | WO 03/057838 A2 | | 7/2003 | |
| WO | WO 2015/044218 A1 | | 4/2015 | |
| WO | WO 2015/136469 A1 | | 9/2015 | |
| WO | WO 2017/046776 A2 | | 3/2017 | |
| WO | WO 2017/149513 A1 | | 9/2017 | |
| WO | WO 2018/033630 A1 | | 2/2018 | |

OTHER PUBLICATIONS

International Search Report and Written Opinion for Application No. PCT/US2019/067387, mailed Apr. 2, 2020.
International Preliminary Report on Patentability for Application No. PCT/US2019/067387, mailed Jul. 2, 2021.
Invitation to Pay Additional Fees for Application No. PCT/US2019/067457, mailed Apr. 1, 2020.
International Search Report and Written Opinion for Application No. PCT/US2019/067457, mailed Jun. 9, 2020.
International Preliminary Report on Patentability for Application No. PCT/US2019/067457, mailed Jul. 2, 2021.
Zhang et al., Generation and characterization of a panel of monoclonal antibodies against distinct epitopes of human CD146. Hybridoma (Larchmt). Oct. 2008;27(5):345-52. doi: 10.1089/hyb.2008.0034.
Extended European Search Report for Application No. 19899845.2, mailed Jan. 24, 2023.
Partial European Search Report for Application No. 19900282.5, mailed Jan. 24, 2023.
Extended European Search Report for Application No. 19900282.5, mailed Apr. 24, 2023.
Bu et al., Anti-CD146 monoclonal antibody AA98 inhibits angiogenesis via suppression of nuclear factor-kappaB activation. Mol Cancer Ther. Nov. 2006;5(11):2872-8. doi: 10.1158/1535-7163.MCT-06-0260.
Fetzko et al., Natural Killer Cells Dually Targeting Soft-Tissue Sarcoma and Its inhibitory Microenvironment Exhibit Enhanced Anti-Tumor Activity. Pediatric Blood and Cancer. Nov. 1, 2021; 68(5): S373.
McGary et al., A fully human antimelanoma cellular adhesion molecule/MUC18 antibody inhibits spontaneous pulmonary metastasis of osteosarcoma cells in vivo. Clin Cancer Res. Dec. 15, 2003;9(17):6560-6.

(Continued)

*Primary Examiner* — M Franco G Salvoza
*Assistant Examiner* — Estella M. Gustilo
(74) *Attorney, Agent, or Firm* — Wolf, Greenfield & Sacks, P.C.

(57) ABSTRACT

Antibodies specific to MUC18 (a.k.a. MCAM or CD146) and uses thereof for therapeutic and diagnostic purposes are provided. Also provided herein are chimeric antigen receptors (CARs) comprising an extracellular antigen-binding fragment that binds MUC18 and immune cells expressing such.

18 Claims, 11 Drawing Sheets

Specification includes a Sequence Listing.

(56) References Cited

OTHER PUBLICATIONS

Mills et al., Fully human antibodies to MCAM/MUC18 inhibit tumor growth and metastasis of human melanoma. Cancer Res. Sep. 1, 2002;62(17):5106-14.
Mohammadi et al., Anti-Metastatic and Anti-Invasion Effects of a Specific Anti-MUC18 scFv Antibody on Breast Cancer Cells. Appl Biochem Biotechnol. Jan. 2017;181(1):379-390. doi: 10.1007/s12010-016-2218-1. Epub Aug. 27, 2016.
Zeng et al., Up-regulation of METCAM/MUC18 promotes motility, invasion, and tumorigenesis of human breast cancer cells. BMC Cancer. Mar. 30, 2011;11:113. doi: 10.1186/1471-2407-11-113.
EP 19899845.2, Jan. 24, 2023, Extended European Search Report.
EP 19900282.5, Jan. 24, 2023, Partial European Search Report.
EP 19900282.5, Apr. 24, 2023, Extended European Search Report.

\* cited by examiner

ANTIBODIES SPECIFIC TO MUC18

This Application is a continuation of International Patent Application No. PCT/US2019/067387, filed Dec. 19, 2019, entitled "ANTIBODIES SPECIFIC TO MUC18". Foreign priority benefits are claimed under 35 U.S.C. § 119 (a)-(d) or 35 U.S.C. § 365 (b) of PCT application number PCT/CN2018/122567, filed Dec. 21, 2018. The entire contents of each of these applications are incorporated herein by reference.

BACKGROUND OF THE INVENTION

MUC18, also known as CD146 or melanoma cell adhesion molecule (MCAM), is a transmembrane glycoprotein that functions primarily in cell adhesion. It is expressed at detectable levels in endothelial cells within vascular tissues, including vascular smooth muscle. Notably, MUC18 is overexpressed in human malignant melanoma, particularly in metastatic lesions and advanced primary tumors. It is therefore of great importance to develop effective MUC18 antagonists, such as anti-MUC18 antibodies for use in both cancer treatment and diagnosis.

SUMMARY OF THE INVENTION

The present disclosure is based, at least in part, on the development of a number of antibodies specific to MUC18. Such antibodies showed high binding affinity to the target MUC18 antigen and/or high inhibitory activity against MUC18$^+$ cells.

Accordingly, one aspect of the present disclosure features an isolated antibody that binds to MUC18 (anti-MUC18 antibody), wherein the antibody binds the same epitope of human MUC18 as a reference antibody, which is CL070325. The structure features of the reference antibody are provided herein.

In some embodiments, an anti-MUC18 antibody may comprises a heavy chain variable region ($V_H$), in which the heavy chain complementary determining region 1 (HC CDR 1), heavy chain complementary determining region 2 (HC CDR 2), and heavy chain complementary determining region 3 (HC CDR 3), collectively, are at least 85% (e.g., at least 90%, at least 95%, at least 98% or more) identical to the HC CDR1, HC CDR2, and HC CDR3 of the reference antibody. In some instances, the antibody may comprise a $V_H$ that includes the same HC CDR1, HC CDR2, and HC CDR3 as one of the reference antibodies noted above. In other embodiments, the anti-MUC18 antibody described herein may comprise a $V_H$ that comprises the HC CDR1, HC CDR2, and HC CDR3, which collectively contain up to 5, 4, 3, 2, or 1 mutation(s) relative to the HC CDR1, HC CDR2, and HC CDR3 of the reference antibody.

Alternatively or in addition, the anti-MUC18 antibody described herein may comprises a light chain variable region ($V_L$), in which the a light chain complementary determining region 1 (LC CDR 1), a light chain complementary determining region 2 (LC CDR 2), and a light chain complementary determining region 3 (LC CDR 3), collectively, are at least 85% (e.g., at least 90%, at least 95%, at least 98% or more) identical to the LC CDR1, LC CDR2, and LC CDR3 of the reference antibody. In some instances, the antibody may comprise the same LC CDR1, LC CDR2, and LC CDR3 as one of the reference antibodies noted above. In other embodiments, the anti-MUC18 antibody described herein may comprise the LC CDR1, LC CDR2, and LC CDR3, which collectively contain up to 5, 4, 3, 2, or 1 mutation(s) relative to the LC CDR1, LC CDR2, and LC CDR3 of the reference antibody.

In some examples, the anti-MUC18 antibody described herein comprises the same heavy chain and/or light chain CDRs as one of the reference antibodies noted above. In some instances, such an anti-MUC18 antibody may comprise the same $V_H$ and/or $V_L$ as the reference antibody.

Any of the anti-MUC18 antibodies described herein may specifically binds to human MUC18. In some instances, the anti-MUC18 antibody may cross-react with human MUC18 and a non-human MUC18, such as a primate MUC18. The antibody may be a human antibody or a humanized antibody. In some examples, it can be a chimeric antibody.

In some embodiments, the anti-MUC18 antibody may be a full-length antibody (e.g., an IgG molecule) or an antigen-binding fragment thereof. Alternatively, it can be a single-chain antibody.

In another aspect, the present disclosure features a nucleic acid or set of nucleic acids (e.g., two nucleic acids), which collectively encodes any of the anti-MUC18 antibodies described herein, and a vector or set of vectors (e.g., two vectors) comprising the nucleic acid(s) coding for the anti-MUC18 antibodies. In some instances, the vector or vector set can be an expression vector(s). Also provided herein are host cells comprising the nucleic acid(s) or vector(s). Further, the present disclosure provides a method for making an anti-MUC18 antibody described herein, comprising culturing the host cell that comprises the vector or vector set comprising coding sequences for the antibody, wherein the coding sequences are in operably linkage to a suitable promoter, and harvesting the antibodies thus produced, for example, from the host cell or the culture medium.

Further, the present disclosure provides a chimeric antigen receptor (CAR), which may comprise: (i) an extracellular domain comprising an antigen binding fragment that binds MUC18, (ii) a transmembrane domain, and (iii) one or more intracellular stimulatory domains. The antigen binding fragment may binds the same epitope of human MUC18 as any of the reference antibodies described herein. In some examples, the antigen binding fragment may comprise the same HC CDRs and/or LC CDRs of any of the reference antibodies. Such an antigen binding fragment may comprise the same $V_H$ and $V_L$ as the reference antibody. In some examples, the antigen binding fragment can be a single chain antibody (scFv).

In any of the CARs described herein, the transmembrane domain may comprise a transmembrane domain derived from CD28 or CD8. Alternatively or in addition, the one or more intracellular stimulatory domains may comprise a signaling domain from CD3ζ and optionally a co-stimulatory signaling domain, which may be from 4-1BB, CD7, CD27, CD28, CD40, OX40, ICOS, GITR, HVEM, TIM1, or LFA-1. Nucleic acids encoding any of the CAR described herein, vectors comprising such, and host cells expressing the CAR are also within the scope of the present disclosure. In some examples, the host cell expressing the CAR is an immune cell such as a T cell.

In yet another aspect, the present disclosure provides a pharmaceutical composition comprising (i) one or more of the anti-MUC18 antibodies described herein, a nucleic acid or set of nucleic acids encoding such, or a host cell expressing any of the CAR constructs described herein, and (ii) a pharmaceutically acceptable carrier.

Moreover, the present disclosure features a method of reducing the number of MUC18$^+$ cells, the method comprising administering to a subject in need thereof an effective amount of any of the pharmaceutical compositions described herein. In some embodiments, the subject may be a human patient has or is suspected of having cancer, for example, an epithelial cancer. Also within the scope of the present disclosure are pharmaceutical compositions as described herein for use in treating any of the target diseases also described herein (e.g., cancer such as an epithelial cancer) or for use in manufacturing a medicament for the treatment of the target disease.

In addition, the present disclosure features a method of detecting presence of MUC18$^+$ cells, the method comprising: (i) contacting a sample suspected of having MUC18$^+$ cells with any of the anti-MUC18 antibodies described herein, which is conjugated with a labeling agent; and (ii) detecting presence MUC18' cells in the sample based on binding of the antibody to cells in the sample. In some instances, the sample is derived from a human patient at risk for or suspected of having a cancer, such as an epithelial cancer.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 2A: a graph showing that anti-MUC18 CAR$^+$ T cells do not induce antigen-dependent cytotoxicity in MUC18$^-$ cells (SKOV-3). FIG. 2B-2E: graphs showing that anti-MUC18 CAR$^+$ T cells are effective in inducing antigen-dependent cytoxicity against MUC18$^+$ cell lines A375, SK-MEL-2, GAK, and HMV-II cells, respectively.

FIG. 3A: a graph showing that anti-MUC18 CAR$^+$ T cells do not induce secretion of IL-2 when co-cultured with MUC18$^-$ cells (SKOV-3). FIG. 3B-3E: graphs showing that anti-MUC18 CAR$^+$ T cells are effective at inducing secretion of IL-2 when co-cultured with MUC18$^+$ cell lines A375, SK-MEL-2, GAK, and HMV-II cells, respectively.

FIG. 4A: a graph showing that anti-MUC18 CAR$^+$ T cells do not induce secretion of IFNγ when co-cultured with MUC18$^-$ cells (SKOV-3). FIG. 4B-4E: graphs showing that anti-MUC18 CAR$^+$ T cells are effective at inducing secretion of IFNγ when co-cultured with MUC18$^+$ cell lines A375, SK-MEL-2, GAK, and HMV-II cells, respectively.

DETAILED DESCRIPTION OF THE INVENTION

Figure 1:
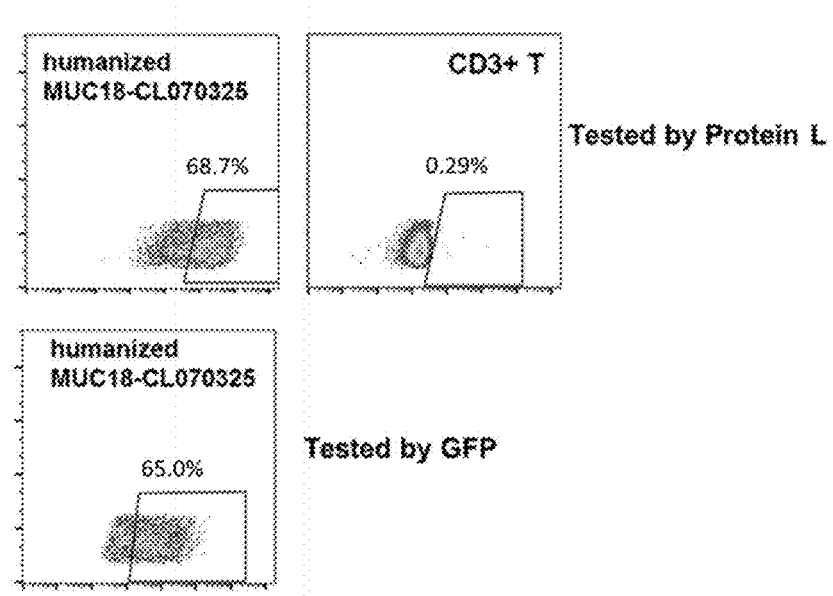
FIG. 1 includes figures showing transduction efficiency of anti-MUC18 CAR lentiviruses into CD3$^+$ T cells.
Figure 2A:
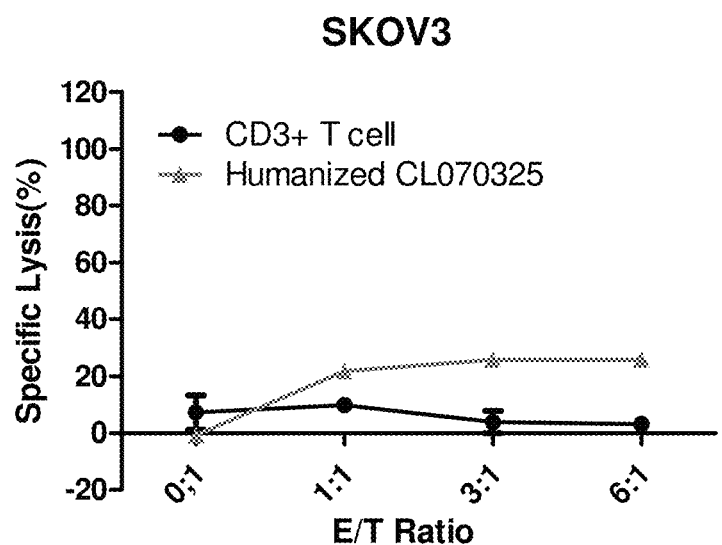
FIGS. 2A-2E include graphs showing the effect of anti-MUC18 CAR$^+$ T cells in inducing antigen-dependent cytoxicity against various MUC18$^+$ cell lines.
Figure 2B:
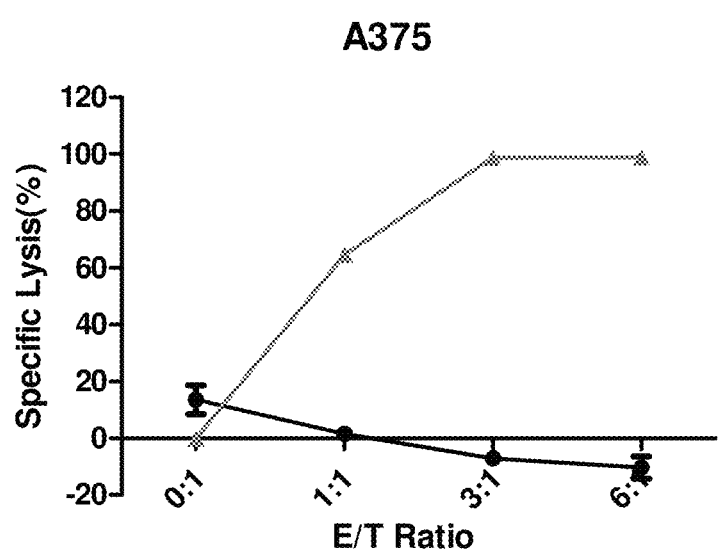
Figure 2C:
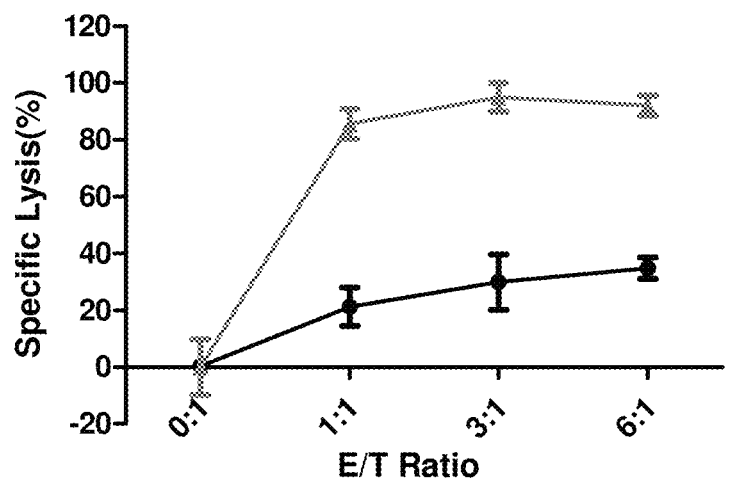
Figure 2D:
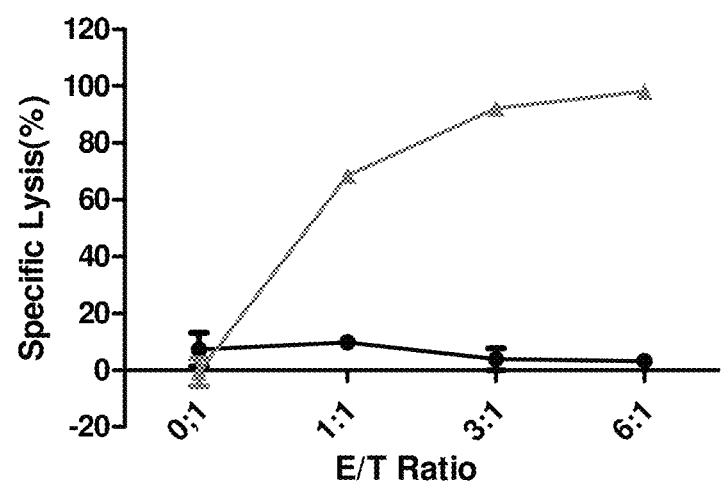
Figure 2E:
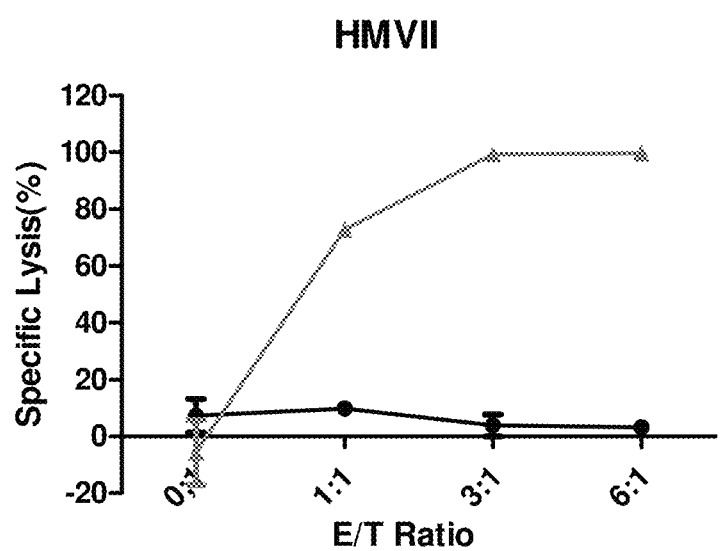
Figure 3A:
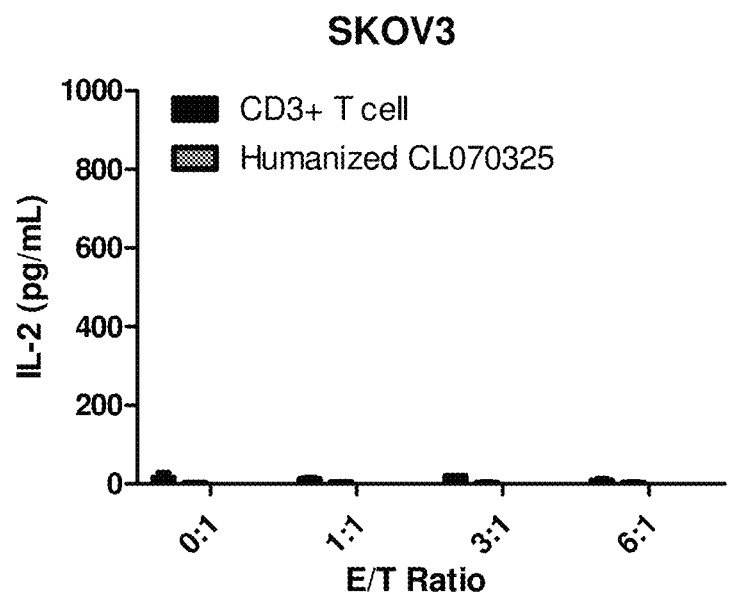
FIGS. 3A-3E include graphs showing the effect of MUC18 CAR$^+$ T cells in inducing secretion of IL-2 when co-cultured with various MUC18$^+$ cell lines.
Figure 3B:
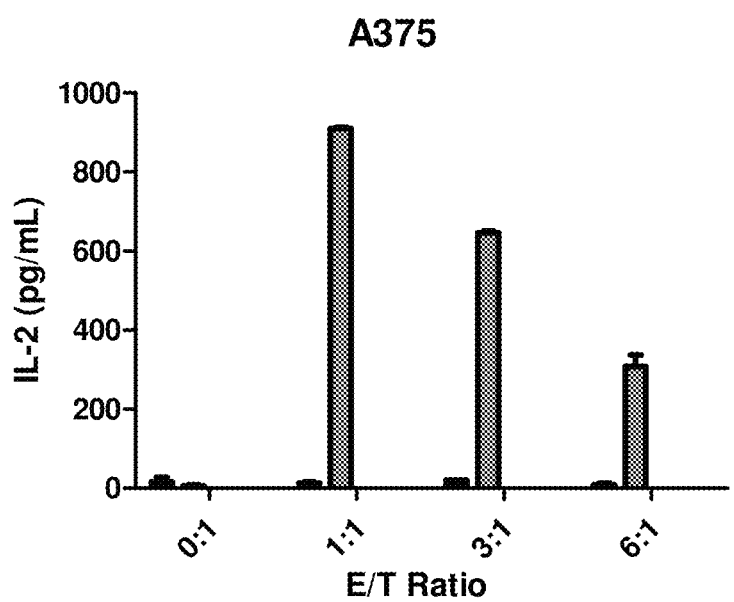
Figure 3C:
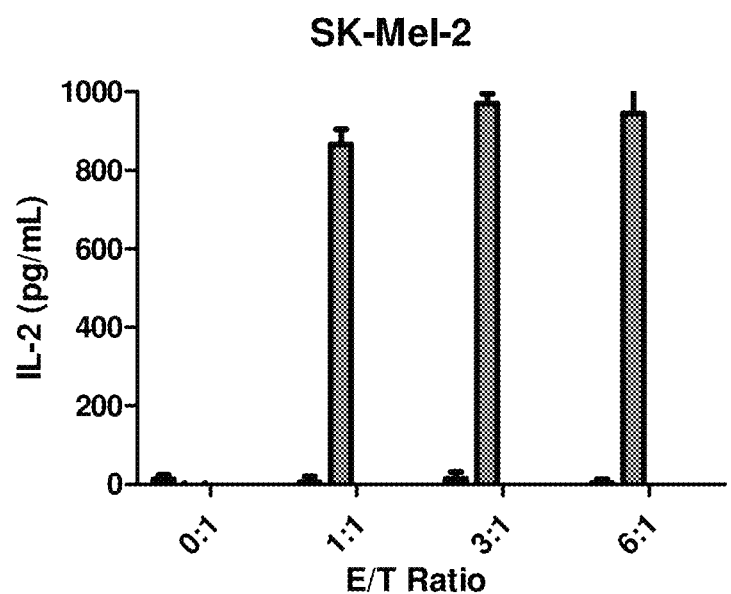
Figure 3D:
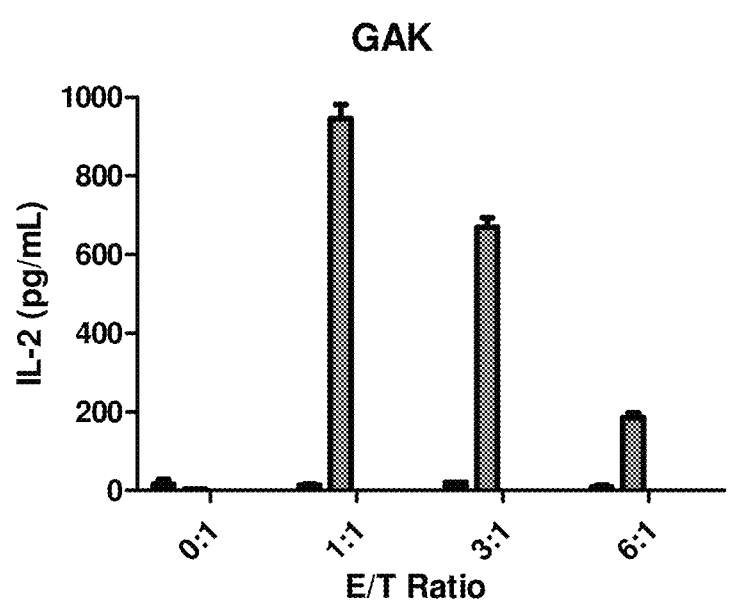
Figure 3E:
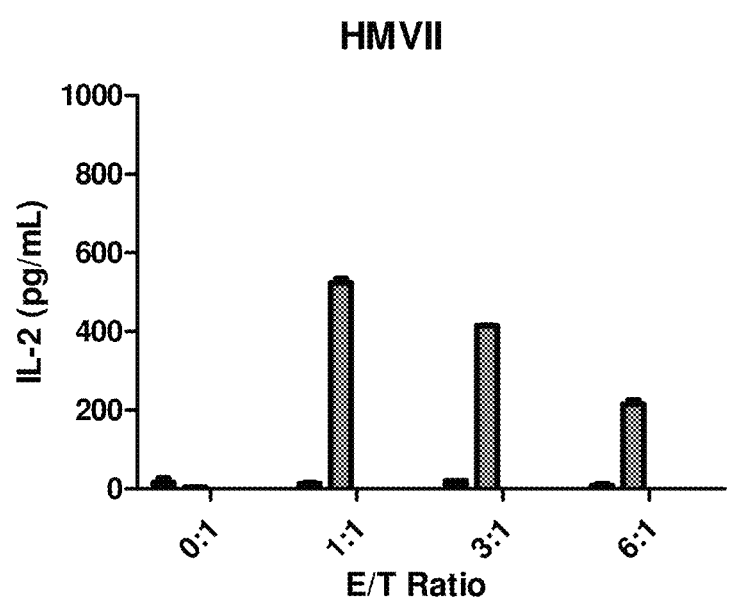
Figure 4A:
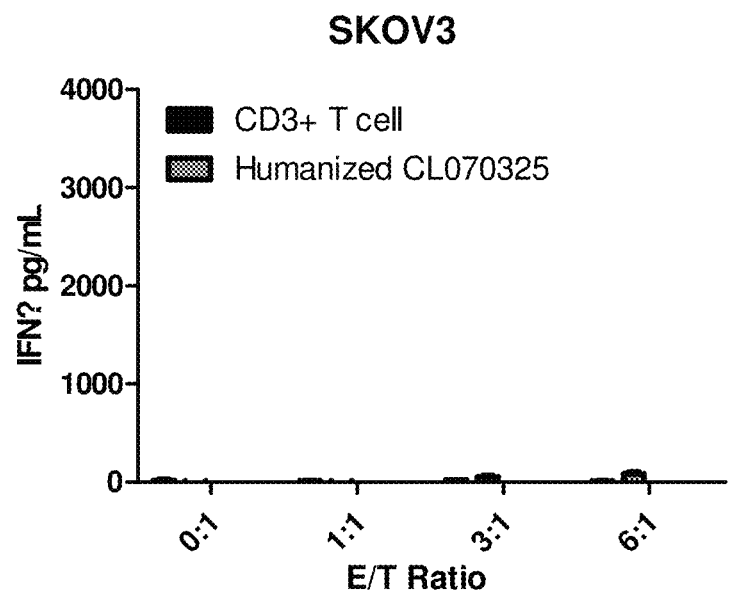
FIGS. 4A-4E include graphs showing the effect of MUC18 CAR$^+$ T cells in inducing secretion of IFNγ when co-cultured with various MUC18$^+$ cell lines.
Figure 4B:
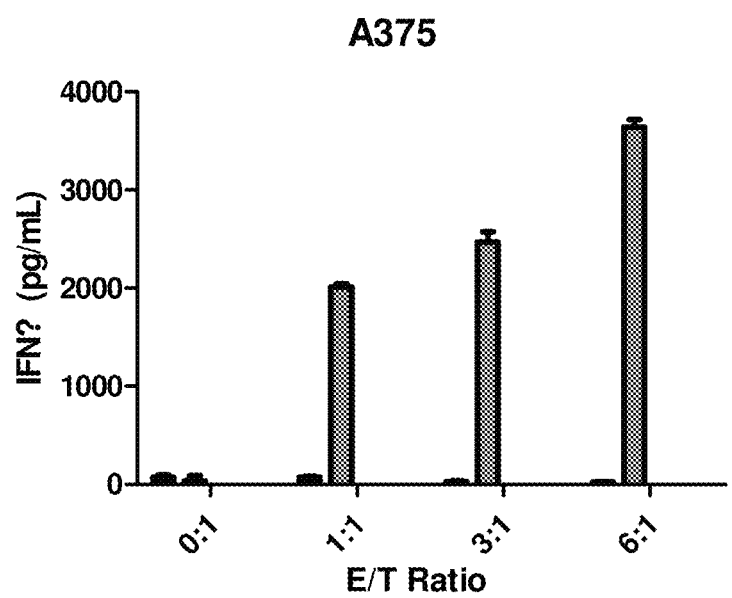
Figure 4C:
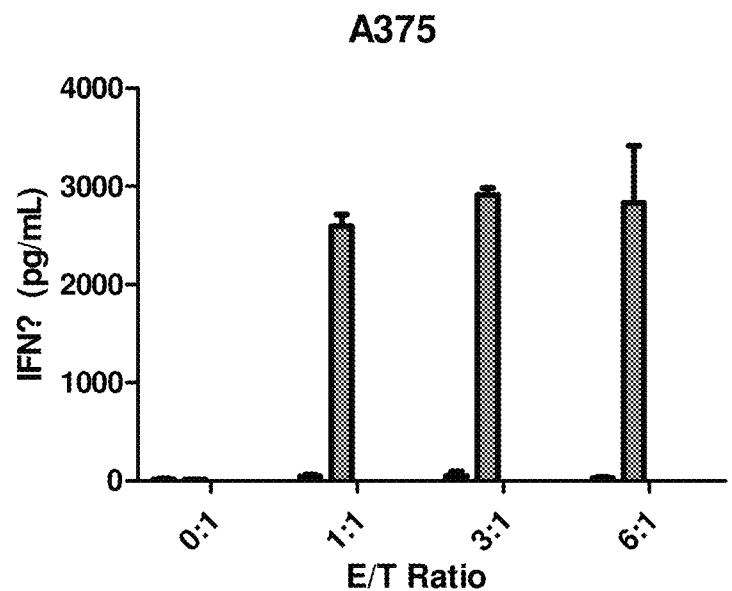
Figure 4D:
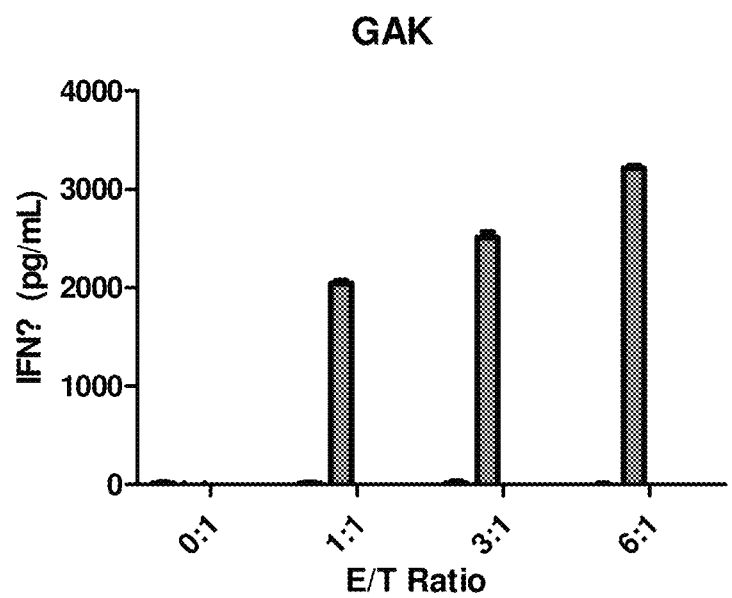
Figure 4E:
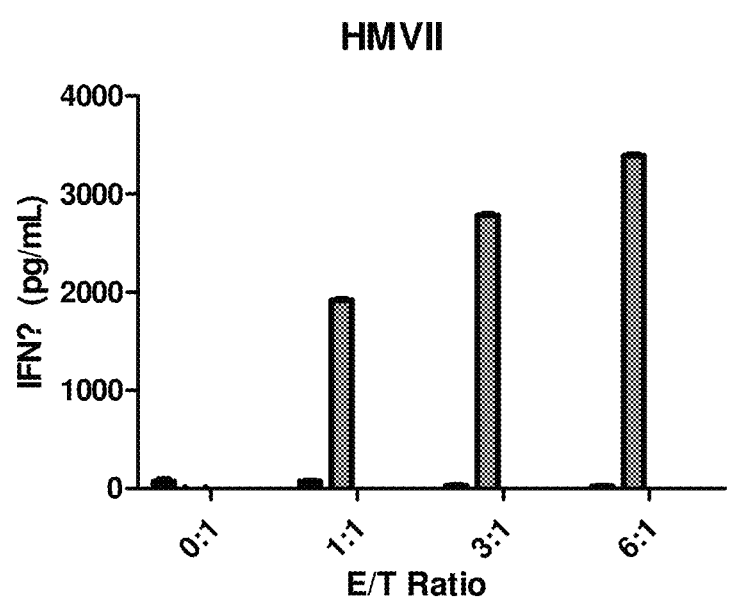

Disclosed herein are a number of anti-MUC18 antibodies, which showed superior features, including high binding affinity to the target MUC18 antigen, and/or high inhibitory activity against MUC18$^+$ cells.

Accordingly, provided herein are antibodies capable of binding to MUC18, nucleic acids encoding such, antibody-drug conjugates (ADCs) and chimeric antigen receptors (CARs) comprising the anti-MUC18 antibodies, and uses thereof for both therapeutic and diagnostic purposes. Also provided herein are kits for therapeutic and/or diagnostic use of the antibodies and/or ADCs and CARs comprising such, as well as methods for producing the anti-MUC18 antibodies.

Antibodies Binding to MUC18

The present disclosure provides antibodies that bind MUC18, which is also known as CD146 or melanoma cell adhesion molecule (MCAM). In humans, MUC18 is encoded by the MCAM gene (NCBI Gene ID: 4162). MUC18 is overexpressed in human malignant melanoma, particularly in metastatic lesions and advanced primary tumors. Resulting from its cellular adhesion functionality, MUC18 may act as a contact point between melanoma cells and cellular elements of the vascular system. This contact might allow melanoma lesions and tumors to permeate the vasculature and for the transmigration of leucocytes during inflammation. MUC18 is additionally thought to trigger tyrosine phosphorylation of FYN and PTK2/FAK1. Further, elevated MUC18 expression levels in melanoma patients have also been demonstrated to be a marker of poor prognosis and survival. Thus this receptor can serve as a target and/or a biomarker for treatment and diagnosis of the target cancer.

Accordingly, the anti-MUC18 antibodies disclosed herein may be used in treating and/or diagnosing a target cancer as described herein, either by itself or being conjugated to other moieties, for example, being conjugated to a therapeutic agent to form an antibody-drug conjugate or being the extracellular antigen-binding domain in a chimeric antigen receptor. Cell therapy targeting MUC18$^+$ cells is also within the present disclosure for eliminating disease cells that expressing cell surface MUC18 (e.g., MUC18$^+$ cancer cells).

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs.

In some embodiments, the anti-MUC18 antibody as described herein can bind and inhibit the activity of MUC18 by at least 50% (e.g., 60%, 70%, 80%, 90%, 95% or greater). The apparent inhibition constant ($Ki^{app}$ or $K_{i,app}$), which provides a measure of inhibitor potency, is related to the concentration of inhibitor required to reduce enzyme activity and is not dependent on enzyme concentrations. The inhibitory activity of an anti-MUC18 antibody described herein can be determined by routine methods known in the art.

The $K_i^{app}$ value of an antibody may be determined by measuring the inhibitory effect of different concentrations of the antibody on the extent of the reaction (e.g., enzyme activity); fitting the change in pseudo-first order rate constant (v) as a function of inhibitor concentration to the modified Morrison equation (Equation 1) yields an estimate of the apparent Ki value. For a competitive inhibitor, the $Ki^{app}$ can be obtained from the y-intercept extracted from a linear regression analysis of a plot of $K_i^{app}$ versus substrate concentration.

$$v = A \cdot \frac{([E] - [I] - K_i^{app}) + \sqrt{([E] - [I] - K_i^{app})^2 + 4[E] \cdot K_i^{app}}}{2} \quad \text{(Equation 1)}$$

Where A is equivalent to $v_o/E$, the initial velocity ($v_0$) of the enzymatic reaction in the absence of inhibitor (I) divided by the total enzyme concentration (E).

In some embodiments, the anti-MUC18 antibody described herein may have a $Ki^{app}$ value of 1000, 900, 800, 700, 600, 500, 400, 300, 200, 100, 50, 40, 30, 20, 19, 18, 17, 16, 15, 14, 13, 12, 11, 10, 9, 8, 7, 6, 5 pM or less for a MUC18 antigen or an antigenic epitope thereof. In some embodiments, the anti-MUC18 antibody may have a lower $Ki^{app}$ for a first target relative to a second target. Differences in $Ki^{app}$ (e.g., for specificity or other comparisons) can be at least 1.5, 2, 3, 4, 5, 10, 15, 20, 37.5, 50, 70, 80, 91, 100, 500, 1000, 10,000 or $10^5$ fold.

The antibodies described herein can be murine, rat, human, or any other origin (including chimeric or humanized antibodies). Such antibodies are non-naturally occurring, i.e., would not be produced in an animal without human act (e.g., immunizing such an animal with a desired antigen or fragment thereof).

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, and/or six), which are altered with respect to the original antibody, which are also termed one or more CDRs "derived from" one or more CDRs from the original antibody. Humanized antibodies may also involve affinity maturation.

In another example, the antibody described herein can be a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-MUC18 antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to a MUC18 antigen or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen. In some embodiments, the anti-MUC18 antibody described herein specifically binds human MUC18. In some examples, its binding activity to a non-human MUC18 antigen is not detectable in a conventional assay or is very low such that it would have no significant biological significance as known to those skilled in the art. In other examples, the anti-MUC18 antibody described herein may cross-react with MUC18 from different species, for example, between human MUC18 and a non-human MUC18 (e.g., MUC18 from an experimental animal such as a non-human primate, mouse, or rat).

As used herein, the term "MUC18", "MCAM", "CD146" or "melanoma cell adhesion molecule" refers to a MUC18 of any suitable species, e.g., human, a non-human mammal such as a non-human primate, or a rodent (e.g., mouse or rat). MUC18 is a transmembrane glycoprotein that functions primarily in cell adhesion. The amino acid sequence of an exemplary human MUC18 is provided below (see also NCBI accession no. NP_006491):

```
                                                            (SEQ ID NO: 3)
  1 mglprlvcaf llaaccccpr vagvpgeaeq papelvevev gstallkcgl sqsqgnlshv 61 dwfsvhkekr tlifrvrqgq gqsepgeyeq rlslqdrgat laltqvtpqd eriflcqgkr 121 prsqeyriql rvykapeepn iqvnplgipv nskepeevat cvgrngypip qviwykngrp 181 lkeeknrvhi qssqtvessg lytlqsilka qlvkedkdaq fycelnyrlp sgnhmkesre 241 vtvpvfypte kvwlevepvg mlkegdrvei rcladgnppp hfsiskqnps treaeeettn 301 dngvlvlepa rkehsgryec qgldldtmis llsepqellv nyvsdvrvsp aaperqegss 361 ltltceaess qdlefqwlre etgqvlergp vlqlhdlkre agggyrcvas vpsipglnrt 421 qlvnvaifgp pwmafkerkv wvkenmvlnl sceasghprp tiswnvngta seqdqdpqrv 481 lstlnvlvtp elletgvect asndlgknts ilflelvnlt tltpdsnttt glststasph 541 transtster klpepesrgv vivavivcil vlavlgavly flykkgklpc rrsgkqeitl 601 ppsrkselvv evksdklpee mgllqgssgd krapgdqgek yidlrh
```

MUC18 molecules from other species were well known in the art and the amino acid sequences thereof can be retrieved from a publically available database, for example, GenBank or NCBI.

In some embodiments, an anti-MUC18 antibody as described herein has a suitable binding affinity for the target antigen (e.g., human MUC18) or antigenic epitopes thereof. As used herein, "binding affinity" refers to the apparent association constant or $K_A$. The $K_A$ is the reciprocal of the dissociation constant ($K_D$). The anti-MUC18 antibody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-MUC18 antibodies described herein have a higher binding affinity (a higher $K_A$ or smaller $K_D$) to human MUC18 as compared to the binding affinity to MUC18 of a different species. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-MUC18 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the anti-MUC18 antibodies described herein bind to the same epitope in a MUC18 antigen (e.g., human MUC18) as one of the reference antibodies provided herein or compete against the reference antibody from binding to the MUC18 antigen. Reference antibodies provided herein include CL070325, the structural features of each of which are provided herein. An antibody that binds the same epitope as a reference antibody described herein may bind to exactly the same epitope or a substantially overlapping epitope (e.g., containing less than 3 non-overlapping amino acid residue, less than 2 non-overlapping amino acid residues, or only 1 non-overlapping amino acid residue) as the reference antibody. Whether two antibodies compete against each other from binding to the cognate antigen can be determined by a competition assay, which is well known in the art. Such antibodies can be identified as known to those skilled in the art, e.g., those having substantially similar structural features (e.g., complementary determining regions), and/or those identified by assays known in the art. For example, competition assays can be performed using one of the reference antibodies to determine whether a candidate antibody binds to the same epitope as the reference antibody or competes against its binding to the MUC18 antigen.

The anti-MUC18 antibodies described herein may comprise a heavy chain variable region ($V_H$), which may comprise (a) a heavy chain complementary determining region 1 (HC CDR 1) as in CL070325 (GYSITSGYY (SEQ ID NO: 4)); (b) a heavy chain complementary determining region 2 (HC CDR2) as in CL070325 (INYGGTN (SEQ ID NO: 5)); (c) a heavy chain complementary determining region 3 (HC CDR3) as in CL070325 (ARGNNDGGFAY (SEQ ID NO: 6)); or (d) a combination of any one of (a)-(c). Alternatively or in addition, the anti-MUC18 antibodies described herein may comprise a light chain variable domain ($V_L$) that comprises a light chain variable region ($V_L$), which comprises (a) a light chain complementary determining region 1 (LC CDR 1) as in CL070325 (SSVSSTY (SEQ ID NO: 7)); (b) a light chain complementary determining region 2 (LC CDR2) as in CL070325 (RAS); (c) a light chain complementary determining region 3 (LC CDR3) as in CL070325 (HQWSGYPYT (SEQ ID NO: 8)); or (d) any combination of (a)-(c).

The heavy chain and light chain CDRs of the reference antibodies provided herein are determined based on the IMGT approach, which is well known in the art. In some instances, the anti-MUC18 antibodies disclosed herein may comprise the same heavy chain and light chain CDRs of any of the reference antibodies disclosed herein. Two antibodies having the same $V_H$ and/or $V_L$ CDRs means that their CDRs are identical when determined by the same approach (e.g., those described herein and/or known in the art).

In some examples, the anti-MUC18 antibodies disclosed herein may comprise the same $V_H$ and/or $V_L$ sequence as CL070325, which are provided below (CDRs in boldface):

CL070325
$V_H$ (SEQ ID NO: 9):
DVQLQESGPGLVKPSQSLSLTCSVT<u>GYSITSGYY</u>WNWIRQFPGNKLEWLG

YI<u>NYGGTN</u>NYNPSLKIRGSITRDTSKNQFFLKLNSVTTEDTATYYC<u>ARGN</u>

<u>NDGGFAY</u>WGQGTLVTVSA $V_L$ (SEQ ID NO: 10):
ENVLTQSPAIVAASLGQKVTMTCSAS<u>SSVSSTY</u>LHWYQQKSGASPKPLLH

<u>RAS</u>NLASGVPARFSGSGSGTSYSLTISSVEAEDDATYYC<u>HQWSGYPYT</u>FG

GGTKLEIK

Also within the scope of the present disclosure are functional variants of any of the reference anti-MUC18 antibodies as disclosed herein (e.g., CL070325). A functional variant can comprise up to 5 (e.g., 4, 3, 2, or 1) amino acid residue variations in one or more of the heavy chain and light chain CDR regions of the reference antibody and binds the same epitope of the MUC18 antigen with substantially similar affinity (e.g., having a $K_D$ value in the same order). In some instances, each of the heavy chain and/or light chain CDR in a functional variant contain no more than 2 amino acid residue variations as relative to the counterpart CDR in the reference antibody. In some examples, each of the heavy chain and/or light chain CDR in a functional variant contain no more than 1 amino acid residue variations as relative to the counterpart CDR in the reference antibody.

In one example, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-MUC18 antibody comprises heavy chain CDRs that, collectively, are at least 80% (e.g., 85%, 90%, 95%, or 98%) identical to the heavy chain CDRs of a reference antibody, and/or light chain CDRs that, collectively, are at least 80% (e.g., 85%, 90%, 95%, or 98%) identical to the light chain CDRs of the reference antibody. In some embodiments, the anti-MUC18 antibody comprises a heavy chain variable region ($V_H$) that is at least 80% (e.g., 85%, 90%, 95%, or 98%) identical to the heavy chain variable region of any of the reference antibody and/or a light chain variable region ($V_L$) that is at least 80% (e.g., 85%, 90%, 95%, or 98%) identical to the light chain variable region of the reference antibody.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

The present disclosure also provides germlined variants of any of the reference anti-MUC18 antibodies disclosed herein. A germlined variant contains one or more mutations in the framework regions as relative to its parent antibody towards the corresponding germline sequence. To make a germline variant, the heavy or light chain variable region sequence of the parent antibody or a portion thereof (e.g., a framework sequence) can be used as a query against an antibody germline sequence database (e.g., bioinfo.org.uk/abs/, vbase2.org, or imgt.org) to identify the corresponding germline sequence used by the parent antibody and amino acid residue variations in one or more of the framework regions between the germline sequence and the parent antibody. One or more amino acid substitutions can then be introduced into the parent antibody based on the germline sequence to produce a germlined variant.

In some instances, the functional variant of a reference antibody disclosed herein is a humanized antibody of the reference antibody. Examples include:

```
Humanized CL070325
V_H (SEQ ID NO: 1):
QVQLQESGPGLVKPSETLSLTCTVSGYSITSGYYWNWIRQFPGNGLEWIG

YINYGGTNNYNPSLKIRVTISRDTSKNQFSLKLSSVTAADTAVYYCARGN

NDGGFAYWGQGTLVTVSS

V_L (SEQ ID NO: 2):
DNQMTQSPSSLSASVGDRVTITCSASSSVSSTYLHWYQQKPGKSPKLLLY

RASNLASGVPSRFSGSGSGTDYTLTISSLQPEDFATYYCHQWSGYPYTFG

GGTKVEIK
```

In some embodiments, the heavy chain of any of the anti-MUC18 antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain). When needed, the anti-MUC18 antibody as described herein may comprise a modified constant region. For example, it may comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the anti-MUC18 antibodies described herein may further comprise a light chain that includes a light chain variable region and optionally, a light chain constant region, which can be any CL known in the art. In some examples, the CL is a kappa light chain. In other examples, the CL is a lambda light chain. Antibody heavy and light chain constant regions are well known in the art, e.g., those provided in the IMGT database (imgt.org) or at vbase2.org/vbstat.php., both of which are incorporated by reference herein.

Preparation of Anti-MUC18 Antibodies

Antibodies capable of binding MUC18 as described herein can be made by any method known in the art. See, for example, Harlow and Lane, (1998) Antibodies: A Laboratory Manual, Cold Spring Harbor Laboratory, New York.

In some embodiments, antibodies specific to a target MUC18 antigen (e.g., human MUC18) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-MUC18 monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the MUC18 activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of MUC18. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

In some embodiments, antibodies capable of binding to a MUC18 antigen can be isolated from an antibody library, for example, a phage display antibody library or a yeast display antibody library. In one example, the anti-MUC18 antibody described herein can be isolated from a monoclonal antibody library, for example, following the methods disclosed in US 2015/0153356, the relevant disclosures of which are incorporated by reference herein for the purposes or subject matter referenced herein.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a MUC18 can be identified from the library following routine procedures. Positive clones can be subjected to further screening to identify those that inhibit MUC18 activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the MUC18 polypeptide have been replaced (swapped) with sequences from a closely related, but antigenically distinct protein. By assessing binding of the antibody to the mutant MUC18, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some examples, an anti-MUC18 antibody is prepared by recombinant technology as exemplified below.

Nucleic acids encoding the heavy and light chain of an anti-MUC18 antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the *Rous sarcoma* virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetR-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-MUC18 antibody, as also described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-MUC18 antibody and the other encoding the light chain of the anti-MUC18 antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-MUC18 antibody as described herein; and vectors (e.g., expression vectors) containing such; and host cells comprising the vectors are within the scope of the present disclosure.

Antibody-Drug Conjugate

The present disclosure also provides antibody-drug conjugates comprising any of the anti-MUC18 antibodies described herein, which is in covalent linkage to a therapeutic agent. The term "antibody-drug conjugate" or "ADC" used herein refers to a conjugate wherein the anti-MUC18 antibody described herein and a therapeutic agent are covalently linked. Generally, this antibody-drug conjugate may include the anti-MUC18 antibody, the therapeutic agent, and optionally a linker between the antibody and the therapeutic agent. The ADC may increase therapeutic effects by delivering the therapeutic agent to a $MUC18^+$ cell, which is targeted by the antibody, in particular, a $MUC18^+$ cancer cell. The antibody-drug conjugate may be prepared by various methods of preparing antibody-drug conjugates, which are known in the art.

The therapeutic agent in the ADC described herein may be a toxin, a chemotherapeutic agent, an antibiotic, ADP-ribosyl transferase, a radioactive isotope or a nucleolytic enzyme. In some instances, the therapeutic agent is a cytotoxic agent. Examples include, but are not limited to, anthracycline, an auristatin (e.g., auristatin E or monomethyl auristatin E (MMAE)), a camptothecin, a combretastain, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and calicheamicin.

In some embodiments, the anti-MUC18 antibody and the therapeutic agent are connected via a linker. Such a linker may be a cleavable linker, for example, cleavable under a certain pH condition (a pH-sensitive linker), cleavable by a protease (a protease-sensitive linker), or cleavable in the presence of glutathione (a glutathione-sensitive linker). In some examples, the linker comprises a protease cleavage site, which may contain 2-5 amino acid residues that are recognizable and/or cleavable by a suitable protease. Such a peptide may comprise naturally-occurring amino acid residues, non-naturally occurring amino acid residues, or a combination thereof. In one example, the peptide linker can be a dipeptide linker. Examples include a valine-citrulline (val-cit) linker, a phenylalanine-lysine (phe-lys) linker, or maleimidocapronic-valine-citruline-p-aminobenzyloxycarbonyl (vc) linker. Alternatively, the linker may be non-cleavable, e.g., a linker comprising optionally substituted alkane or thioether.

In some examples, the linker may comprise a functional group that can form a covalent bond with the antibody. Exemplary functional groups include, but are not limited to, a maleimide group, an iodoacetamide group, a vinyl sulfone group, an acrylate group, an acrylamide group, an acrylonitrile group, or a methacrylate group. In some instances, the linker can contain one or more reactive amines include, but are not limited to, acetyl-lysine-valine-citrulline-p-amino-benzyloxycarbonyl (AcLys-VC-PABC) or amino PEG6-propionyl. See, e.g., WO2012/059882. Other exemplary linkers include Sulfosuccinimidyl-4-[Nmaleimidomethyl] cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N terminus).

In some examples, the linker may comprise a molecular spacer, for example, a moiety of Formula I:

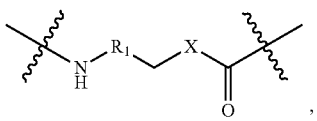

in which $R_1$ can be optionally substituted $C_{1-6}$ alkyl (e.g., $C_{1-3}$ alkyl), optionally substituted phenyl, optionally substituted $C_{2-6}$ alkylene, optionally substituted $C_{2-6}$ alkenylene, optionally substituted $C_{2-6}$ alkynylene, or optionally substituted triazole; and/or X can be O, S, or N.

Methods for conjugating cytotoxic agent or other therapeutic agents to antibodies were known in the art and have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, (2005), and Gentle et al., Bioconjug. Chem. 15:658-663, (2004). Reactive cysteine residues engineered at specific sites of antibodies for specific drug conjugation with defined stoichiometry have also been described. See, e.g., Junutula et al., Nature Biotechnology, 26:925-932, (2008). Conjugation using an acyl donor glutamine-containing tag and/or an endogenous glutamine made reactive by polypeptide engineering in the presence of transglutaminase and an amine, for example, a cytotoxic agent modified with a reactive amine, is also described in WO2012/059882, Strop et al., Chem. Biol. 20(2):161-167 (2013), and Farias et al., Bioconjug. Chem. 25(2):245-250 (2014). The relevant disclosures of such publications are herein incorporated by reference for the purpose and subject matter referenced therein.

Chimeric Antigen Receptor (CAR) and Immune Cells Expressing Such

The present disclosure also features chimeric antigen receptors targeting MUC18 and immune cells expressing such. Chimeric antigen receptors (CARs) as disclosed herein are artificial cell-surface receptors that redirect binding specificity of immune cells (e.g., T cells) expressing such to MUC18$^+$ cells, such as epithelium-derived cancer cells, thereby eliminating the target disease cells via, e.g., the effector activity of the immune cells. A CAR construct often comprises an extracellular antigen binding domain fused to at least an intracellular signaling domain. Cartellieri et al., J Biomed Biotechnol 2010:956304, 2010. The extracellular antigen binding domain, which can be a single-chain antibody fragment (scFv), is specific to a MUC18 antigen and the intracellular signaling domain can mediate a cell signaling that lead to activation of immune cells. As such, immune cells expressing a CAR construct specific to MUC18 can bind to diseased cells (e.g., tumor cells) expressing MUC18, leading to activation of the immune cells and elimination of the diseased cells.

Any of the anti-MUC18 antibodies described herein can be used to produce the CAR constructs also described herein. For example, the $V_H$ and $V_L$ domains of an anti-MUC18 antibody can be fused to the intracellular signaling domain(s) to produce a CAR construct using the conventional recombinant technology. In some examples, the $V_H$ and $V_L$ domains of an anti-MUC18 are connected via a peptide linker to form a scFv fragment.

The CAR construct disclosed herein may comprise one or more intracellular signaling domains. In some examples, CAR comprises an intracellular signaling domain that includes an immunoreceptor tyrosine-based activation motif (ITAM). Such an intracellular signaling domain may be from CD3ζ. In addition, the CAR construct may further comprise one or more co-stimulatory signaling domains, which may be from a co-stimulatory receptor, for example, from 4-1BB (CD137), CD7, CD27, CD28, CD40, OX40, ICOS, GITR, HVEM, TIM1, or LFA-1.

The CAR construct disclosed herein may further comprise a transmembrane-hinge domain, which can be obtained from a suitable cell-surface receptor, for example, CD28 or CD8.

Also provided are isolated nucleic acid molecules and vectors encoding any of the anti-MUC18 CARs as disclosed herein, and host cells, such as host immune cells (e.g., T cells and natural killer cells), comprising the nucleic acid molecules or vectors. Immune cells expressing anti-MUC18 CARs, which comprises a MUC18-specific antibody binding fragment, can be used for the treatment of cancers that express MUC18. Thus, also provided herein are methods of treating a subject with MUC18$^+$ cancer by selecting a subject with a cancer that expresses MUC18, and administering to the subject a therapeutically effective amount of the immune cells expressing the MUC18-targeted CARs.

Pharmaceutical Compositions

The anti-MUC18 antibodies, the encoding nucleic acids or nucleic acid sets, vectors comprising such, or host cells comprising the vectors, as described herein, as well as the ADCs comprising the anti-MUC18 antibodies and/or immune cells expressing MUC18-targeting CARs, can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids, or the ADCs), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, the encoding nucleic acid(s), or the ADCs may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Methods of Treatment and Diagnosis

Any of the anti-MUC18 antibodies, the encoding nucleic acids or nucleic acid sets, vectors comprising such, the ADCs comprising the anti-MUC18 antibodies, and immune cells (e.g., T cells or NK cells) expressing MUC18-targeting CARs, as described herein, are useful for inhibiting and/or eliminating MUC18$^+$ disease cells, such as MUC18$^+$ cancer cells, thereby benefiting treatment of a disease or disorder associated with the MUC18$^+$ disease cells.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder associated with $MUC18^+$ disease cells. In some embodiments, the $MUC18^+$ disease cells are cancer cells, for example, epithelial cancer cells (i.e., derived from epithelial cells). Examples include, but are not limited to, ovarian cancer cells, breast cancer cells, renal cancer cells, lung cancer cells, colorectal cancer cells, and brain cancer cells. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is reduced MUC18 activity or the activity of $MUC18^+$ cells. Determination of whether an amount of the antibody or other therapeutic agents comprising such (e.g., ADC or CAR-T cells) achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the anti-MUC18 antibodies or ADCs comprising such as described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is a decrease in thrombosis. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the antibodies described herein are administered to a subject in need of the treatment at an amount sufficient to inhibit the activity of one or both of the target antigen by at least 20% (e.g., 30%, 40%, 50%, 60%, 70%, 80%, 90% or greater) in vivo. In other embodiments, the antibodies are administered in an amount effective in reducing the activity level of a target antigens by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:

16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

When immune cells expressing a MUC18-targeting CAR are used for disease treatment, patients can be treated by infusing therapeutically effective doses of such immune cells such as T lymphocytes or NK cells in the range of about $10^5$ to $10^{10}$ or more cells per kilogram of body weight (cells/Kg). The infusion can be repeated as often and as many times as the patient can tolerate until the desired response is achieved. The appropriate infusion dose and schedule will vary from patient to patient, but can be determined by the treating physician for a particular patient. Typically, initial doses of approximately $10^6$ cells/Kg will be infused, escalating to $10^8$ or more cells/Kg. IL-2 can be co-administered to expand infused cells. The amount of IL-2 can about $1-5\times10^6$ international units per square meter of body surface.

In some embodiments, more than one antibody, or a combination of an antibody and another suitable therapeutic agent, may be administered to a subject in need of the treatment. The antibody, ADCs and/or CAR-T cells comprising such, can also be used in conjunction with other agents that serve to enhance and/or complement the effectiveness of the agents.

Treatment efficacy for a target disease/disorder can be assessed by methods well-known in the art.

Any of the anti-MUC18 antibodies described herein may also be used for detecting the presence or level of MUC18+ cells in a sample. Such a diagnostic assay may be performed in vitro or in vivo.

For diagnostic uses, an anti-MUC18 antibody as described herein may be conjugated with a detectable label (e.g., an imaging agent such as a contrast agent) for diagnostic purposes, either in vivo or in vitro. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

In one example, an anti-MUC18 antibody as described herein can be attached to a detectable label, which is a compound that is capable of releasing a detectable signal, either directly or indirectly, such that the aptamer can be detected, measured, and/or qualified, in vitro or in vivo. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the aptamer, directly or indirectly, by conventional methods.

In some embodiments, the detectable label is an agent suitable for imaging MUC18+ cells in vivo, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99m}$Tc Oxidronate, $^{99m}$Tc Pentetate, $^{99m}$Tc Pertechnetate, $^{99m}$Tc Sestamibi, $^{99m}$Tc Sulfur Colloid, $^{99m}$Tc Tetrofosmin, Thallium-201, and Xenon-133. The reporting agent can also be a dye, e.g., a fluorophore, which is useful in detecting a disease mediated by MUC18+ cells in tissue samples.

To perform a diagnostic assay in vitro, an anti-MUC18 antibody can be brought in contact with a sample suspected of containing MUC18+ cells. The antibody and the sample may be incubated under suitable conditions for a suitable period to allow for binding of the antibody to the MUC18 antigen. Such an interaction can then be detected via routine methods, e.g., ELISA or FACS. To perform a diagnostic assay in vivo, a suitable amount of anti-MUC18 antibodies, conjugated with a label, can be administered to a subject in need of the examination. Presence of the labeled antibody can be detected based on the signal released from the label by routine methods.

Kits for Use in Treatment and Diagnosis

The present disclosure also provides kits for use in inhibiting and/or eliminating MUC18' disease cells and thus alleviating diseases/disorders associated with such disease cells. Such kits can include one or more containers comprising an anti-MUC18 antibody, an ADC comprising such, or immune cells expressing MUC18-targeting CAR polypeptide, e.g., any of those described herein.

In some embodiments, the kit can comprise instructions for use in accordance with any of the methods described herein. The included instructions can comprise a description of administration of the anti-MUC18 antibody, the ADC, or the immune cells to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, an ADC, or immune cells, to an individual at risk of the target disease.

The instructions relating to the use of an anti-MUC18 antibody, an ADC comprising such, or immune cells expressing MUC18-targeting CAR, generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with MUC18+ cells, such as epithelial cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-MUC18 antibody, an ADC comprising such, or immune cells expressing MUC18-targeting CAR as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Also provided herein are kits for use in detecting MUC18+ cells in a sample. Such a kit may comprise any of the anti-MUC18 antibodies described herein. In some instances, the anti-MUC18 antibody can be conjugated with a detectable label as those described herein. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

Alternatively or in addition, the kit may comprise a secondary antibody capable of binding to anti-MUC18 antibody. The kit may further comprise instructions for using the anti-MUC18 antibody for detecting MUC18±.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Generation of Anti-MUC18 Antibodies

Reagents and General Methods

Hybridoma cell culture medium (PFHM-II Protein-Free Hybridoma Medium; #12040077) was purchased from Thermo Fisher.

RNAs were isolated using standard protocols and the TRIzol Reagent from Thermo Fisher (#15596018). Resultant cDNA molecules were generated using the cDNA synthesis kit (PrimeScript II 1st strand cDNA synthesis kit; #6210A) from Takara. Antibody V-region amplification was performed using Premix Taq (#RR901A) from Takara. Standard PCR primer sets (Ig-Primer Sets #TB326) were obtained from Novagen. Genes were cloned into pET28a (Novagen; #69864) using standard techniques, including use of EcoRI, HindIII, SalI, and T4 Ligase (all from NEB). QIAEX II Gel Extraction Kit (QIAgen #20021) was utilized to purify some, but not all, oligonucleotide molecules.

A375, SK-Mel-2, GAK, HMVII, and SK-OV-3 cell cultures were maintained in vitro as independent monolayer cultures at 37° C. in an atmosphere of 5% $CO_2$. These tumor cells were passaged regularly, as needed.

Immunization to Generate Anti-MUC18 Antibodies

CL070325 was generated using immunization methodologies. Briefly, Balc/c mice were immunized six times with an intra-muscular injection of a recombinant MUC18 protein (purchased from ACRO BioSystems; amino acid residues 24-559).

Production of Antibody Clones

Individual hybridoma clones were cultured in a T25 flask with 10 mL hybridoma cell culture medium (PFHM-II Protein-Free Hybridoma Medium). Cells were grown at 37° C. until 80% confluent. Culture medium was then removed and cells were twice washed with 1×PBS. TRIzol reagent (1 mL vol.) was added directly to the flask and cells were lysed by pipette-mixing. The cell lysate was then recovered from the T25 flask and total RNA was isolated using standard methods. RNA concentrations were subsequently measured with a Nanodrop 2000 (Thermo Fisher). Strand cDNA was then generated from the isolated RNA according to the Takara PrimeScript II 1st strand cDNA synthesis kit protocol. Amplification of the hybridoma V-region of the resultant cDNA was then performed following Novagen user protocol TB326. Primer pairs, as shown in Table 3 below, were used for amplification:

TABLE 3

Primers for amplifying nucleic acids encoding anti-MUC18 antibodies

| | Primer | Sequence (5' to 3') | SEQ ID NO: |
|---|---|---|---|
| 1 | MuIgVH5'-A | GGGAATTCATGRASTTSKGGYTMARCTKGRTTT | 11 |
| 2 | MuIgVH5'-B | GGGAATTCATGRAATGSASCTGGGTYWTYCTCTT | 12 |
| 3 | MuIgVH5'-C1 | ACTAGTCGACATGGACTCCAGGCTCAATTTAGTTTTCCT | 13 |
| 4 | MuIgVH5'-C2 | ACTAGTCGACATGGCTGTCYTRGBGCTGYTCYTCTG | 14 |
| 5 | MuIgVH5'-C3 | ACTAGTCGACATGGVTTGGSTGTGGAMCTTGCYATTCCT | 15 |
| 6 | MuIgVH5'-D1 | ACTAGTCGACATGAAATGCAGCTGGRTYATSTTCTT | 16 |
| 7 | MuIgVH5'-D2 | ACTAGTCGACATGGRCAGRCTTACWTYYTCATTCCT | 17 |
| 8 | MuIgVH5'-D3 | ACTAGTCGACATGATGGTGTTAAGTCTTCTGTACCT | 18 |
| 9 | MuIgVH5'-E1 | ACTAGTCGACATGGGATGGAGCTRTATCATSYTCTT | 19 |
| 10 | MuIgVH5'-E2 | ACTAGTCGACATGAAGWTGTGGBTRAACTGGRT | 20 |
| 11 | MuIgVH5'-E3 | ACTAGTCGACATGGRATGGASCKKIRTCTTTMTCT | 21 |
| 12 | MuIgVH5'-F1 | ACTAGTCGACATGAACTTYGGGYTSAGMTTGRTTT | 22 |
| 13 | MuIgVH5'-F2 | ACTAGTCGACATGTACTTGGGACTGAGCTGTGTAT | 23 |
| 14 | MuIgVH5'-F3 | ACTAGTCGACATGAGAGTGCTGATTCTTTTGTG | 24 |
| 15 | MuIgVH5'-F4 | ACTAGTCGACATGGATTTTGGGCTGATTTTTTTATTG | 25 |
| 16 | MuIgMVH3'-1 | CCCAAGCTTACGAGGGGGAAGACATTTGGGAA | 26 |
| 17 | MuIgGVH3'-2 | CCCAAGCTTCCAGGGRCCARKGGATARACIGRTGG | 27 |
| 18 | MuIgkVL5'-A | GGGAATTCATGRAGWCACAKWCYCAGGTCTTT | 28 |
| 19 | MuIgkVL5'-B | GGGAATTCATGGAGACAGACACACTCCTGCTAT | 29 |
| 20 | MuIgkVL5'-C | ACTAGTCGACATGGAGWCAGACACACTSCTGYTATGGGT | 30 |
| 21 | MuIgkVL5'-D1 | ACTAGTCGACATGAGGRCCCCTGCTCAGWTTYTTGGIWTCTT | 31 |
| 22 | MuIgkVL5'-D2 | ACTAGTCGACATGGGCWTCAAGATGRAGTCACAKWYYCWGG | 32 |
| 23 | MuIgkVL5'-E1 | ACTAGTCGACATGAGTGTGCYCACTCAGGTCCTGGSGTT | 33 |
| 24 | MuIgkVL5'-E2 | ACTAGTCGACATGTGGGGAYCGKTTTYAMMCTTTTCAATTG | 34 |
| 25 | MuIgkVL5'-E3 | ACTAGTCGACATGGAAGCCCCAGCTCAGCTTCTCTTCC | 35 |
| 26 | MuIgkVL5'-F1 | ACTAGTCGACATGAGIMMKTCIMTTCAITTCYTGGG | 36 |
| 27 | MuIgkVL5'-F2 | ACTAGTCGACATGAKGTHCYCIGCTCAGYTYCTIRG | 37 |
| 28 | MuIgkVL5'-F3 | ACTAGTCGACATGGTRTCCWCASCTCAGTTCCTTG | 38 |
| 29 | MuIgkVL5'-F4 | ACTAGTCGACATGTATATATGTTTGTTGTCTATTTCT | 39 |
| 30 | MuIgkVL5'-G1 | ACTAGTCGACATGAAGTTGCCTGTTAGGCTGTTGGTGCT | 40 |
| 31 | MuIgkVL5'-G2 | ACTAGTCGACATGGATTTWCARGTGCAGATTWTCAGCTT | 41 |
| 32 | MuIgkVL5'-G3 | ACTAGTCGACATGGTYCTYATVTCCTTGCTGTTCTGG | 42 |
| 33 | MuIgkVL5'-G4 | ACTAGTCGACATGGTYCTYATVTTRCTGCTGCTATGG | 43 |
| 34 | MuIgkVL3'-1 | CCCAAGCTTACTGGATGGTGGGAAGATGGA | 44 |

TABLE 3-continued

Primers for amplifying nucleic acids
encoding anti-MUC18 antibodies

| Primer | Sequence (5' to 3') | SEQ ID NO: |
|---|---|---|
| 35 MuIgIVL5'-A | GGGAATTCATGGCCTGGAYTYCWCTYWTMYTCT | 45 |
| 36 MuIgIVL3'-1 | CCCAAGCTTAGCTCYTCWGWGGAIGGYGGRAA | 46 |

PCR products were checked with 1% Agarose gel. Positive PCR products were recovered using QIAgen gel extraction kits and subsequently cloned into pET28a vector using restriction enzymes (from NEB) corresponding to the primer sequence. pET28a vectors with PCR product insertion were transformed into DH5a bacterial cells and cultured on Ampicillin-positive agar plates. Each bacterial clone was sent for Sanger sequencing using the MuIgGVH3'-2, MuIgkVL3'-1 or MuIglVL3'-1 primers. Obtained sequences were compared for consistence to confirm target $V_H$ and $V_L$ sequences, respectively. $V_H$ and $V_L$ sequences were then analyzed on the IGMT database (imgt.org/) to provide the V-region, Frame and CDR elements of $V_H$ and $V_L$.

In Vitro Binding Activity to MUC18

CL070325 was tested in an antigen binding assay using ELISA titration experiments. Antibody was incubated with varying concentrations of recombinant MUC18 protein (rProtein). CL070325 bound MUC18 with a 1.56 nM binding affinity.

Example 2: Preparation and In Vitro Evaluation of Anti-MUC18 CAR⁺ T Cells

Humanized CL070325 anti-MUC18 antibodies ($V_H$ and $V_L$) were inserted into a chimeric antigen receptor vector in frame with a CD8 hinge region, a CD8 transmembrane region, an intracellular domain of the co-stimulator 4-1BB, and an intracellular domain of CD3ζ. The vector further comprises a EF1α promotor. Nucleic acids encoding the anti-MUC18 CAR⁺ were transfected using lentiviral packaging into 293T cells. Human CD3+ T cells were then activated and transduced with lentivirus to produce anti-MUC18 CAR+ T cells. Following production of the anti-MUC18 CAR⁺ T cells as described above, the transduction efficiency for each CAR construct was determined using FACS (FIG. 1). T cell populations transduced with humanized CL070325 CAR comprised >65% CAR⁺ cells.

The ability of anti-MUC18 CAR⁺ T cells to induce antigen-dependent cytotoxicity and IFNγ secretion in MUC18⁺ melanoma cell lines (A375, SK-MEL-2, GAK, and HMV-II cells) was tested. SKOV-3 cells, which have low expression levels of MUC18, were utilized as a negative control cell line. Each melanoma cell line was dosed with anti-MUC18 CAR⁺ T cells or a control (CD3 T cells) at varying ratios of T cells (Effector cells)-to-Target cells.

After incubation of the T cells with the target cells, specific lysis/cytotoxicity of the target cells were assessed using standard methods (FIGS. 2A-2E). In all MUC18⁺ cell lines, the addition of anti-MUC18 CAR⁺ T cells induced antigen-dependent cytotoxicity at and above a ratio of 1:1 T cell:Target cell. The control experiments (incubation with CD3 T cells without a CAR) led to no significant induction of specific cytotoxicity.

During the same dosing experiments, the ability of anti-MUC18 CAR⁺ T cells to induce secretion of interleukin-2 (IL-2) and interferon gamma (IFNγ) by the target cells was assessed using standard methods (FIGS. 3A-3E and FIGS. 4A-4E). In all MUC18⁺ cell lines, the addition of anti-MUC18 CAR⁺ T cells induced high levels of IL-2 and IFNγ at and above a ratio of 1:1 T cell:Target cell. The control experiments (incubation with CD3 T cells without a CAR) led to no significant secretion of IL-2 or IFNγ.

Example 3: In Vivo Evaluation of Anti-MUC18 CAR⁺ T Cells

A375 Xenograft Model

Mice were injected subcutaneously with A375 melanoma cells. On Days 4 (mean tumor size ~100 mm³) and 8 following injection of A375 cells, mice were injected subcutaneously with either CD3 T cells (control) or humanized CL070325 CAR⁺ T cells at a concentration of 6×10⁶ cells/mouse. The CAR⁺ T cell population comprised ~50% CAR⁺ cells. Tumor volume was measured two times per week from day of treatment initiation.

Figure 5A:
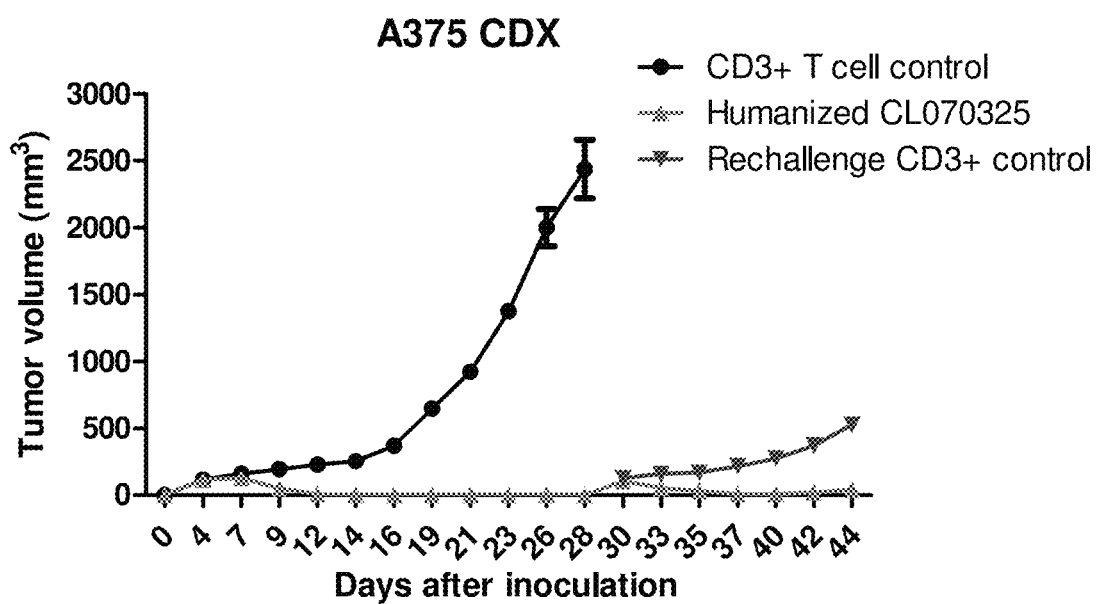
FIG. 5A includes a graph showing the ability of anti-MUC18 CAR$^+$ T cells to reduce tumor volume in an A375 xenograft mouse model, relative to control T cells.

Mice treated with the anti-MUC18 CAR⁺ T cells population had a reduction in tumor growth relative to the mice treated with control T cells (FIG. 5A). Surprisingly, by Day 12, the anti-MUC18 CAR⁺ T cells had essentially eliminated the A375 melanoma tumor.

GAK Xenograft Model

Mice were injected subcutaneously with GAK melanoma cells. On Days 4 (mean tumor size ~150 mm³) and 8 following injection of GAK cells, mice were injected subcutaneously with either CD3 T cells (control) or humanized CL070325 CAR⁺ T cells at a concentration of 6×10⁶ cells/mouse. The CAR⁺ T cell population comprised ~50% CAR⁺ cells. Tumor volume was measured three times per week from day of treatment initiation.

Figure 5B:
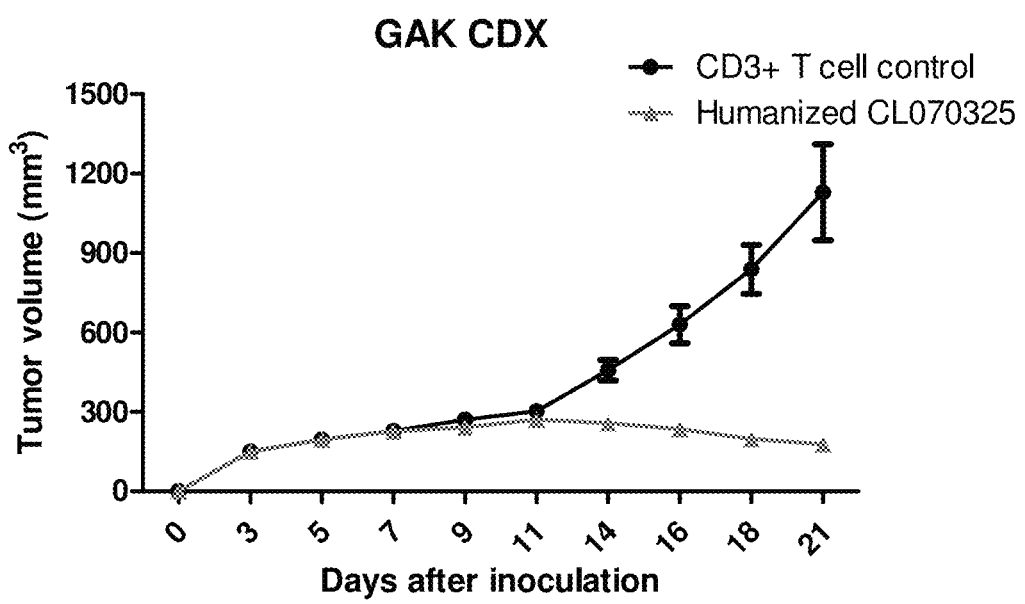
FIG. 5B includes a graph showing the ability of anti-MUC18 CAR$^+$ T cells to reduce tumor volume in an GAK xenograft mouse model, relative to control T cells.

Mice treated with the anti-MUC18 CAR⁺ T cells population had a reduction in tumor growth relative to the mice treated with control T cells (FIG. 5B). Surprisingly, the anti-MUC18 CAR⁺ T cells induced a sustained reduction in the GAK melanoma tumor through Day 21 of the experiment.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. An isolated antibody that binds to human MUC18, wherein the antibody comprises a heavy chain variable region ($V_H$) comprising a heavy chain complementary determining region 1 (HC CDR1) of the amino acid sequence of SEQ ID NO: 4, a HC CDR2 of the amino acid sequence of SEQ ID NO: 5, and a HC CDR3 of the amino acid sequence of SEQ ID NO: 6, and a light chain variable region ($V_L$) comprising a light chain CDR1 (LC CDR1) of the amino acid sequence of SEQ ID NO: 7, a LC CDR2 of the amino acid sequence of RAS, and a LC CDR3 of the amino acid sequence of SEQ ID NO: 8.

2. The isolated antibody of claim 1, wherein the $V_H$ is at least 85% identical to the amino acid sequence of SEQ ID NO: 9, and/or wherein the $V_L$ is at least 85% identical to the amino acid sequence of SEQ ID NO: 10.

3. The isolated antibody of claim 2, wherein the isolated antibody comprises the $V_H$ of the amino acid sequence of SEQ ID NO: 9, and/or the $V_L$ of the amino acid sequence of SEQ ID NO: 10.

4. The isolated antibody of claim 1, wherein the antibody specifically binds to human MUC18.

5. The isolated antibody of claim 1, wherein the antibody comprises a $V_H$ set forth as SEQ ID NO: 1 and/or a $V_L$ set forth as SEQ ID NO: 2.

6. A nucleic acid or set of nucleic acids, which collectively encodes the antibody of claim 1.

7. A vector or set of vectors comprising the nucleic acid or set of nucleic acids of claim 6.

8. A host cell comprising the vector or vector set of claim 7.

9. A pharmaceutical composition comprising (i) the antibody of claim 1; and (ii) a pharmaceutically acceptable carrier.

10. A method of reducing the number of MUC18+ cells, the method comprising administering to a subject in need thereof an effective amount of the pharmaceutical composition of claim 9.

11. A method of detecting presence of $MUC18^+$ cells, the method comprising: i. contacting a sample suspected of having $MUC18^+$ cells with the antibody of claim 1, wherein the antibody is conjugated with a labeling agent; and ii. detecting presence $MUC18^+$ cells in the sample based on binding of the antibody to cells in the sample.

12. The isolated antibody of claim 1, wherein the antibody cross-reacts with human MUC18 and a non-human MUC18.

13. The isolated antibody of claim 12, wherein the non-human MUC18 is a primate MUC18.

14. The isolated antibody of claim 1, wherein the antibody is a full-length antibody or an antigen-binding fragment thereof.

15. The isolated antibody of claim 1, wherein the antibody is an IgG molecule.

16. The isolated antibody of claim 1, wherein the antibody is a humanized antibody or a chimeric antibody.

17. The isolated antibody of claim 1, wherein the antibody is a single-chain antibody.

18. The vector or set of vectors of claim 7, wherein the vector or set of vectors is an expression vector or set of expression vectors.

* * * * *

SEQUENCE LISTING

```
<160> NUMBER OF SEQ ID NOS: 46

<210> SEQ ID NO 1
<211> LENGTH: 118
<212> TYPE: PRT
<213> ORGANISM: Homo sapiens

<400> SEQUENCE: 1

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Tyr Ser Ile Thr Ser Gly
            20                  25                  30

Tyr Tyr Trp Asn Trp Ile Arg Gln Phe Pro Gly Asn Gly Leu Glu Trp
            35                  40                  45

Ile Gly Tyr Ile Asn Tyr Gly Gly Thr Asn Asn Tyr Asn Pro Ser Leu
 50                  55                  60

Lys Ile Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Asn Asn Asp Gly Gly Phe Ala Tyr Trp Gly Gln Gly Thr
            100                 105                 110

Leu Val Thr Val Ser Ser
            115

<210> SEQ ID NO 2
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 2

Asp Asn Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Ser Thr
            20                  25                  30

Tyr Leu His Trp Tyr Gln Gln Lys Pro Gly Lys Ser Pro Lys Leu Leu
            35                  40                  45

Leu Tyr Arg Ala Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys His Gln Trp Ser Gly Tyr Pro
                85                  90                  95

Tyr Thr Phe Gly Gly Gly Thr Lys Val Glu Ile Lys
            100                 105

<210> SEQ ID NO 3
<211> LENGTH: 646
<212> TYPE: PRT
<213> ORGANISM: Artificial Sequence
<220> FEATURE:
<223> OTHER INFORMATION: Synthetic Polypeptide

<400> SEQUENCE: 3

Met Gly Leu Pro Arg Leu Val Cys Ala Phe Leu Leu Ala Ala Cys Cys
 1               5                  10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
 50                  55                  60

Val His Lys Glu Lys Arg Thr Leu Ile Phe Arg Val Arg Gln Gly Gln
 65                  70                  75                  80

Gly Gln Ser Glu Pro Gly Glu Tyr Glu Gln Arg Leu Ser Leu Gln Asp
```

```
                85                  90                  95
Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
            115                 120                 125

Gln Leu Arg Val Tyr Lys Ala Pro Glu Pro Asn Ile Gln Val Asn
            130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
            210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
            275                 280                 285

Pro Ser Thr Arg Glu Ala Glu Glu Thr Thr Asn Asp Asn Gly Val
            290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Gly Gln
            370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Pro Pro Trp
            420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510
```

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
        530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Ser Glu Leu
            595                 600                 605

Val Val Glu Val Lys Ser Asp Lys Leu Pro Glu Glu Met Gly Leu Leu
        610                 615                 620

Gln Gly Ser Ser Gly Asp Lys Arg Ala Pro Gly Asp Gln Gly Glu Lys
625                 630                 635                 640

Tyr Ile Asp Leu Arg His
                645

<210> SEQ ID NO 4
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 4

Gly Tyr Ser Ile Thr Ser Gly Tyr Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Ile Asn Tyr Gly Gly Thr Asn
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 6

Ala Arg Gly Asn Asn Asp Gly Gly Phe Ala Tyr
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 7

Ser Ser Val Ser Ser Thr Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 8

His Gln Trp Ser Gly Tyr Pro Tyr Thr
1               5

<210> SEQ ID NO 9
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 9

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Leu Gly Tyr Ile Asn Tyr Gly Thr Asn Asn Tyr Asn Pro Ser Leu
    50                  55                  60

Lys Ile Arg Gly Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Asn Asn Asp Gly Gly Phe Ala Tyr Trp Gly Gln Gly Thr
            100                 105                 110

Leu Val Thr Val Ser Ala
        115

<210> SEQ ID NO 10
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 10

Glu Asn Val Leu Thr Gln Ser Pro Ala Ile Val Ala Ala Ser Leu Gly
1               5                   10                  15

Gln Lys Val Thr Met Thr Cys Ser Ala Ser Ser Ser Val Ser Ser Thr
            20                  25                  30

Tyr Leu His Trp Tyr Gln Gln Lys Ser Gly Ala Ser Pro Lys Pro Leu
        35                  40                  45

Leu His Arg Ala Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys His Gln Trp Ser Gly Tyr Pro
                85                  90                  95

Tyr Thr Phe Gly Gly Gly Thr Lys Leu Glu Ile Lys
            100                 105

<210> SEQ ID NO 11
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 11
gggaattcat grasttskgg ytmarctkgr ttt                        33

<210> SEQ ID NO 12
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 12
gggaattcat graatgsasc tgggtywtyc tctt                       34

<210> SEQ ID NO 13
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 13
actagtcgac atggactcca ggctcaattt agttttcct                  39

<210> SEQ ID NO 14
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 14
actagtcgac atggctgtcy trgbgctgyt cytctg                     36

<210> SEQ ID NO 15
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 15
actagtcgac atggvttggs tgtggamctt gcyattcct                  39

<210> SEQ ID NO 16
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 16
actagtcgac atgaaatgca gctggrtyat sttctt                     36

<210> SEQ ID NO 17
<211> LENGTH: 36
<212> TYPE: DNA
<213> ORGANISM: Artificial Sequence
<220> FEATURE:
<223> OTHER INFORMATION: Synthetic Polynucleotide -continued

<400> SEQUENCE: 17
actagtcgac atggrcagrc ttacwtyytc attcct                     36

<210> SEQ ID NO 18
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 18
actagtcgac atgatggtgt taagtcttct gtacct                     36

<210> SEQ ID NO 19
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 19
actagtcgac atgggatgga gctrtatcat sytctt                     36

<210> SEQ ID NO 20
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 20
actagtcgac atgaagwtgt ggbtraactg grt                        33

<210> SEQ ID NO 21
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: n is inosine

<400> SEQUENCE: 21
actagtcgac atggratgga sckknrtctt tmtct                      35

<210> SEQ ID NO 22
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 22
actagtcgac atgaacttyg ggytsagmtt grttt                      35

<210> SEQ ID NO 23
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 23

```
actagtcgac atgtacttgg gactgagctg tgtat                          35

<210> SEQ ID NO 24
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 24
actagtcgac atgagagtgc tgattctttt gtg                            33

<210> SEQ ID NO 25
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 25
actagtcgac atggattttg ggctgatttt ttttattg                       38

<210> SEQ ID NO 26
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 26
cccaagctta cgaggggggaa gacatttggg aa                            32

<210> SEQ ID NO 27
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (30)..(30)
<223> OTHER INFORMATION: n is inosine

<400> SEQUENCE: 27
cccaagcttc cagggrccar kggataracn grtgg                          35

<210> SEQ ID NO 28
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 28
gggaattcat gragwcacak wcycaggtct tt                             32

<210> SEQ ID NO 29
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 29
gggaattcat ggagacagac acactcctgc tat                            33
```

```
<210> SEQ ID NO 30
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 30
actagtcgac atggagwcag acacactsct gytatgggt                              39

<210> SEQ ID NO 31
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (37)..(37)
<223> OTHER INFORMATION: n is inosine

<400> SEQUENCE: 31
actagtcgac atgaggrccc ctgctcagwt tyttggnwtc tt                          42

<210> SEQ ID NO 32
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 32
actagtcgac atgggcwtca agatgragtc acakwyycwg g                           41

<210> SEQ ID NO 33
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 33
actagtcgac atgagtgtgc ycactcaggt cctggsgtt                              39

<210> SEQ ID NO 34
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 34
actagtcgac atgtggggay cgktttyamm cttttcaatt g                           41

<210> SEQ ID NO 35
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 35
actagtcgac atggaagccc cagctcagct tctcttcc                               38

<210> SEQ ID NO 36
<211> LENGTH: 36
<212> TYPE: DNA
```

<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: n is inosine
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (28)..(28)
<223> OTHER INFORMATION: n is inosine

<400> SEQUENCE: 36
actagtcgac atgagnmmkt cnmttcantt cytggg                36

<210> SEQ ID NO 37
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (34)..(34)
<223> OTHER INFORMATION: n is inosine

<400> SEQUENCE: 37
actagtcgac atgakgthcy cngctcagyt yctnrg                36

<210> SEQ ID NO 38
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 38
actagtcgac atggtrtccw casctcagtt ccttg                 35

<210> SEQ ID NO 39
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 39
actagtcgac atgtatatat gtttgttgtc tatttct               37

<210> SEQ ID NO 40
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 40
actagtcgac atgaagttgc ctgttaggct gttggtgct             39

<210> SEQ ID NO 41
<211> LENGTH: 39

```
<212> TYPE: DNA
<213> ORGANISM: Artificial Sequence
<220> FEATURE:
<223> OTHER INFORMATION: Synthetic Polynucleotide

<400> SEQUENCE: 41
actagtcgac atggatttwc argtgcagat twtcagctt                                39

<210> SEQ ID NO 42
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 42
actagtcgac atggtyctya tvtccttgct gttctgg                                  37

<210> SEQ ID NO 43
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 43
actagtcgac atggtyctya tvttrctgct gctatgg                                  37

<210> SEQ ID NO 44
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 44
cccaagctta ctggatggtg ggaagatgga                                          30

<210> SEQ ID NO 45
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 45
gggaattcat ggcctggayt ycwctywtmy tct                                      33

<210> SEQ ID NO 46
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: n is inosine

<400> SEQUENCE: 46
cccaagctta gctcytcwgw gganggyggr aa                                       32
```